United States Patent
McArthur

(10) Patent No.: US 10,143,716 B2
(45) Date of Patent: *Dec. 4, 2018

(54) PAWPAW AND/OR PEACH DERIVED COMPOSITION

(71) Applicant: PHOENIX EAGLE COMPANY PTY LTD, Mount Lawley, W.A. (AU)

(72) Inventor: Thomas James McArthur, Hervey Bay (AU)

(73) Assignee: PHOENIX EAGLE COMPANY PTY LTD, Mount Lawley (AU)

(*) Notice: Subject to any disclaimer, the term of this patent is extended or adjusted under 35 U.S.C. 154(b) by 477 days.

This patent is subject to a terminal disclaimer.

(21) Appl. No.: 14/178,420

(22) Filed: Feb. 12, 2014

(65) Prior Publication Data

US 2014/0335209 A1 Nov. 13, 2014

Related U.S. Application Data

(63) Continuation of application No. 13/491,829, filed on Jun. 8, 2012, now Pat. No. 8,685,473, which is a continuation of application No. 11/713,206, filed on Mar. 1, 2007, now Pat. No. 8,216,615, which is a continuation of application No. 10/521,380, filed as application No. PCT/AU03/00931 on Jul. 22, 2003, now abandoned.

(30) Foreign Application Priority Data

Jul. 23, 2002 (AU) .................... 2002950308

(51) Int. Cl.
| | | |
|---|---|---|
| A61K 36/18 | (2006.01) |
| A61K 36/88 | (2006.01) |
| A61K 8/92 | (2006.01) |
| A61K 8/97 | (2017.01) |
| A61K 36/22 | (2006.01) |
| A61K 36/42 | (2006.01) |
| A61K 36/45 | (2006.01) |
| A61K 36/73 | (2006.01) |
| A61K 36/736 | (2006.01) |
| A61K 36/752 | (2006.01) |
| A61K 36/81 | (2006.01) |
| A61Q 19/00 | (2006.01) |
| A61Q 19/08 | (2006.01) |
| A61K 36/185 | (2006.01) |
| A61K 36/54 | (2006.01) |
| A61Q 7/00 | (2006.01) |
| A61Q 17/04 | (2006.01) |
| A61Q 19/10 | (2006.01) |
| A23L 19/00 | (2016.01) |
| A61Q 19/02 | (2006.01) |

(52) U.S. Cl.
CPC .............. *A61K 36/88* (2013.01); *A23L 19/09* (2016.08); *A61K 8/922* (2013.01); *A61K 8/97* (2013.01); *A61K 36/185* (2013.01); *A61K 36/22* (2013.01); *A61K 36/42* (2013.01); *A61K 36/45* (2013.01); *A61K 36/54* (2013.01); *A61K 36/73* (2013.01); *A61K 36/736* (2013.01); *A61K 36/752* (2013.01); *A61K 36/81* (2013.01); *A61Q 7/00* (2013.01); *A61Q 17/04* (2013.01); *A61Q 19/00* (2013.01); *A61Q 19/004* (2013.01); *A61Q 19/007* (2013.01); *A61Q 19/08* (2013.01); *A61Q 19/10* (2013.01); *A61K 2800/72* (2013.01); *A61K 2800/75* (2013.01); *A61Q 19/005* (2013.01); *A61Q 19/02* (2013.01)

(58) Field of Classification Search
CPC ....... A61K 36/185; A61K 36/18; A61K 36/88
USPC .................................................. 424/725, 777
See application file for complete search history.

(56) References Cited

U.S. PATENT DOCUMENTS

| | | | |
|---|---|---|---|
| 1,997,616 A | 4/1935 | Wallerstein et al. |
| 2,059,541 A | 11/1936 | Thompson et al. |
| 2,500,670 A | 3/1950 | Dunkley |
| 3,126,287 A | 3/1964 | Finkle |
| 3,274,072 A | 9/1966 | Burdick |
| 4,105,783 A | 8/1978 | Yu et al. |

(Continued)

FOREIGN PATENT DOCUMENTS

| | | |
|---|---|---|
| CN | 1090767 | 8/1994 |
| CN | 1141792 | 2/1997 |

(Continued)

OTHER PUBLICATIONS

"Africa'S Garden—Avocado Oil & Herb," 2002, wwww.africasgarden.com/HistoricalUses.html.
"Alban Muller International—Products of Nature," www.albanmuller.fr/anglais/catalogue/classiques/default.asp?milieu=cata0315.html, copyright 2013.
"Cosmetic Ingredients." DERMAdoctor. Nov. 2002. pp. 1-9, http://www.dermadoctor.com/pages/newslettr108.asp.
"Healthpoint—Accuzyme Ointment," 2006, Healthpoint, Ltd.
"Hot Springs," Chemical Dictionary 2 Condensed Version, (1963). (English translation).
"Pacifica Natural Skincare Products—Natural Skincare Formulas," 2002, www.pacificanaturalskin.com/bodyhtml.
"Passion Fruit Jam Small-Scale Production," Intermediate Technology Development Group, Jan. 2004.

(Continued)

*Primary Examiner* — Christopher R Tate

(74) *Attorney, Agent, or Firm* — Parker Highlander PLLC

(57) ABSTRACT

There is provided a process for making a composition suitable for topical application comprising the steps of a) heating at least one fruit and/or vegetable pulp to up to a temperature in the range of about 40° C. to 100° C.; b) mixing between 1 and 40% w/w of a mild base with the heated fruit and/or vegetable pulp. There is also provided a fruit and/or vegetable derived composition suitable for topical application prepared by the above process. There is further provided a fruit and/or vegetable derived composition comprising at least one fruit and/or vegetable-derived pulp and a mild base, said composition having a pH in the range of about 7.5 to about 9.5.

14 Claims, No Drawings

(56) References Cited

U.S. PATENT DOCUMENTS

| | | | |
|---|---|---|---|
| 4,118,271 A * | 10/1978 | Oku | D21C 1/06 162/31 |
| 4,459,285 A | 7/1984 | Grollier et al. | |
| 4,505,902 A | 3/1985 | Millard | |
| 4,941,990 A | 7/1990 | McLaughlin | |
| 4,950,493 A | 8/1990 | Kobes et al. | |
| 5,304,374 A * | 4/1994 | Graves | A23L 19/07 424/725 |
| 5,436,022 A | 7/1995 | Chiang et al. | |
| 5,705,166 A | 1/1996 | Arve | |
| 5,500,241 A | 3/1996 | Balasingham | |
| 5,529,769 A | 6/1996 | Cho et al. | |
| 5,547,988 A | 8/1996 | Yu et al. | |
| 5,560,953 A | 10/1996 | Greenwell et al. | |
| 5,578,312 A * | 11/1996 | Parrinello | A61K 8/0212 424/401 |
| 5,609,875 A | 3/1997 | Hadas | |
| 5,665,413 A | 9/1997 | Rossiter | |
| 5,708,038 A | 1/1998 | Davis | |
| 5,804,168 A | 9/1998 | Murad | |
| 5,811,101 A | 9/1998 | Waltman | |
| 5,879,665 A | 3/1999 | Fuller | |
| 5,882,666 A | 3/1999 | Averill et al. | |
| 5,922,374 A | 7/1999 | Daury et al. | |
| 5,932,230 A | 8/1999 | DeGrate | |
| 5,935,383 A * | 8/1999 | Sun | D21H 21/20 162/146 |
| 5,939,457 A | 8/1999 | Miser | |
| 5,972,344 A | 10/1999 | Edwards | |
| 5,989,559 A | 11/1999 | Edwards | |
| 5,993,876 A | 11/1999 | Bertocchi | |
| 6,013,260 A | 1/2000 | Edwards | |
| 6,042,841 A | 3/2000 | Alaluf et al. | |
| 6,063,382 A | 5/2000 | Nakajima et al. | |
| 6,096,295 A | 8/2000 | Fuller | |
| 6,147,054 A | 11/2000 | De Paoli Ambrosi | |
| 6,190,664 B1 | 2/2001 | Dampeirou | |
| 6,261,603 B1 | 7/2001 | McElwain | |
| 6,309,675 B1 | 10/2001 | Sobczak | |
| 6,361,804 B2 | 3/2002 | Singh-Verma | |
| 6,368,654 B1 | 4/2002 | Evans et al. | |
| 6,379,716 B2 | 4/2002 | Santhanam et al. | |
| 6,383,495 B1 | 5/2002 | Ramakrishna et al. | |
| 6,416,769 B1 | 7/2002 | Vromen | |
| 6,423,747 B1 | 7/2002 | Landendorger et al. | |
| 6,426,081 B1 | 9/2002 | Chong | |
| 6,445,076 B1 | 9/2002 | Shimizu et al. | |
| 6,447,820 B1 | 9/2002 | Niazi | |
| 6,455,057 B1 | 9/2002 | Barrett et al. | |
| 6,623,779 B1 | 9/2003 | Huxsoll et al. | |
| 6,630,163 B1 | 10/2003 | Murad | |
| 6,730,333 B1 | 10/2004 | Garrity et al. | |
| 6,800,292 B1 | 10/2004 | Murad | |
| 6,855,359 B2 | 2/2005 | Khare | |
| 7,153,536 B2 | 12/2006 | Kuhns et al. | |
| 7,166,281 B2 | 1/2007 | Kennedy | |
| 7,198,811 B2 | 4/2007 | Paliyath et al. | |
| 7,228,793 B2 | 6/2007 | Ling et al. | |
| 7,288,265 B1 * | 10/2007 | Rolf | A61K 9/7038 424/443 |
| 2001/0021401 A1 | 9/2001 | Sharma et al. | |
| 2002/0034553 A1 | 3/2002 | Zayas | |
| 2003/0211176 A1 * | 11/2003 | Suzuki | A23L 2/52 424/725 |
| 2004/0022818 A1 | 2/2004 | Cho et al. | |
| 2005/0031573 A1 | 2/2005 | Cho et al. | |
| 2005/0048145 A1 | 3/2005 | Azik | |
| 2005/0053564 A1 | 3/2005 | Lieberman | |
| 2005/0249720 A1 | 11/2005 | Perez | |

FOREIGN PATENT DOCUMENTS

| | | |
|---|---|---|
| DE | 198 53 998 | 5/2000 |
| EP | 0 111 895 | 6/1984 |
| EP | 0 923 937 | 6/1999 |
| EP | 1 217 987 | 7/2002 |
| FR | 2 441 343 | 6/1980 |
| GB | 732983 | 7/1955 |
| GB | 1 403 062 | 8/1975 |
| GB | 2 232 587 | 12/1990 |
| GB | 2 341 317 | 3/2000 |
| JP | 2000-319163 | 11/2000 |
| JP | 2001-039823 | 2/2001 |
| JP | 2001-122723 | 5/2001 |
| JP | 2001-226248 | 8/2001 |
| JP | 2001-322943 | 11/2001 |
| JP | 2002-020256 | 1/2002 |
| JP | 2002020256 A * | 1/2002 |
| JP | 2003-171303 | 4/2002 |
| JP | 2002-128651 | 5/2002 |
| WO | WO 1989/010750 | 11/1989 |
| WO | WO 1997/002807 | 1/1997 |
| WO | WO 1997/034568 | 9/1997 |
| WO | WO 2000/064472 | 11/2000 |
| WO | WO 2000/074698 | 12/2000 |
| WO | WO 2001/085182 | 11/2001 |
| WO | WO 2001/095873 | 12/2001 |

OTHER PUBLICATIONS

"Pawpaw ointment," Retrieved from the internet. <http://www.lucaspawpaw.com.au/>. Jun. 23, 2006. 4 pages.
"Potato," Potato-Herb Profile and Information, pp. 1-3, http://viablehealth.com/botanical/mgmh/p/potato65.html, copyright 2005.
"Skin Therapy Letter," May 1998, pp. 1-5, vol. 3, No. 5, http://www.derm.ucb.ca/skintherapy/stl0305.html.
"Squamous and Basel Cell Carcinoma Treatment Strategies Part 1, Topicalinfo" The Skin Cancer Treatment Toolbox, Aug. 2002, pp. 1-13, http://www.topicalinfo.org/Treatment.html.
21 CFR 184.1721; FDA, Food Substances Affirmed as Generally Recognized as Safe: Sodium Acetate, (Apr. 2010).
Alley, L., "Saving summer in a jar is what it's all about at the county fair," the San Diego Union-Tribune, San Diego, California, Jun. 12, 2002, p. E1, pp. 1-6 of ProQuest.
Blackstone. R., "A gift to avoid the Yule budget jam," The Province, Vancouver, B.C. Nov. 17, 1993, p. B. 8, pp. 1-2 ProQuest.
Buchard, "The Pawpaw Chase," The Washington Post, Sep. 17, 1999, pp. 40. Retrieved from Proquest. pp. 1-6 of Proquest.
Burckhardt, A., "Quick Pickles and Jams: Some up-to-date ideas on how to preserve a bit of the past," Minneapolis Star and Tribune, Minneapolis, Minn; Jul. 16, 1986, p. 3 T, pp. 1-6 ProQuest.
Chem 206, PKa Table 1, PKa's of Inorganic and Oxo-Acids, http://www.chem.wisc.edu/areas/reich/pkatable/index.htm, accessed Feb. 7, 2008.
Code of Federal Regulations, Title 21, Parts 100-114, revised as of Apr. 1, 2005.
Cummins et al., "Cutaneous Malignant Melanoma," Mayo Clinic Proceedings, Rochester, Apr. 2006, vol. 81, Issue 4, p. 500, 8 pages (pp. 1-10 of ProQuest).
Curry & Chilli Cookbook, "Prawn, Pawpaw and Chilli Salad," Bay Books, an imprint of Murdoch Books Ply Limited., Millers Point NSW, 2000, Australia, 2008, pp. 75, 112.
De La Cruz Medina, J., et al., "Importance of the Post-Production System for Paw Paw in Developing Countries," Instituto Technologico de Veracruz, edited by AGS1/FAO, Mexico, http://fao.org/inpho/content/compend/text/CH22_01.htm, accessed Feb. 14, 2014.
Edwards-Jones, Valerie, et al., "What's new in burn microbiology? James Laing Memorial Prize Essay 2000," Burns, 2003, pp. 15-24, vol. 29, Elsevier Science Ltd and ISBI.
Examination Report for Canadian Patent Application No. 2,492,461, dated Mar. 11, 2010, pp. 1-2.
Exhibit 1. Mohammad Najmul Ghani Khan; Khazaain-al-Advia, vol. I (2oth century Ad), Nadeem Yunus Printer/Sheikh Mohd Basheer & Sons, Lahore, 1911 AD p. 625. Formuation ID: NA2/220AD2. Formulation Name: Taraavish-e-Shaakh-e Angoor, written in Sanskrit, including English language summary/translation. Total of 3 pages.

(56) References Cited

OTHER PUBLICATIONS

Exhibit 10. Govt of India; Sahastrayoga—translated by D.V. Panditarao: Central Council for Research in Ayurevda & Siddha. New Deli, 1990. [This book contains back references from 1000 B.C. To 2oth century] p. 289. Forumlation ID: VS/3694. Formulation Name: Vranabhairavatailam, written in Sanskrit, including English language summary/translation. Total of 7 pages.
Exhibit 2. Ziya Al-Din Abdullah lbn Al-Baitar; Al-Jaam'e-li-Mufradaat-al-Advia-wal-Aghzia, vol. II (13th century AD), Matba Amra, Cairo, Egypt, 1874 AD p. 152-153. Formulation ID: JA3/222. Formulation Name: Zabeeb, written in Sanskrit, including English language summary/translation. Total of 3 pages.
Exhibit 3. Mohammad Najmul Ghani Khan; khazaain-al-Advia, vol. I (2oth century AD), Nadeem Yunus Printer/Sheikh Mohad Basher & Sons, Hahore, 1911 AD p. 625. Formulation ID: NA2/220AD. Formulation Name: Zimaad Bara-e-Waram-e-Khusyatain, written in Sanskrit, including English language summary/translation. Total of 2 pages.
Exhibit 4. Mohammad Najmul Ghani Khan; Khazaain-al-Advia, vol. I (2oth century AD), Nadeem Yunus Printer/Sheikh Mohd Baseer & Sons, Lahore, 1911 AD p. 627-628. Formulation ID: NA2/224. Fonnulation Name: Anannas, written in Sanskrit, including English language summary/translation. Total of 3 pages.
Exhibit 5. Mohammad Najmul Ghani Khan; Khazaain-al-Advia, vol. II (20th century AD). Nadeem Yunus Printer/Sheikh Mohd Basheer & Sons, Lahore 1911 AD p. 695. Formulation including English summary/translation. Total of 2 pages.
Exhibit 6. Ziya AL-Din Abdullah Ibn Al-Jaam'eli-Murfradaat-al-Advia-wal-Aghzia, vol. II (13th century AD) Matba Amra, Cairo, Egypt, 1874 AD p. 112. Formulation ID: JA31272. Formulation Name: Roghn-e Maghz Tukhm Zard Aaloo, written in Sanskrit, including English summary/translation. Total of 3 pages.
Exhibit 7. Kaiyadeva; Kaiyadevanighantau—(Pathyapathyavibodhakah). Edited and translated by P.V. Sharma and Guru Prasad Sharma, Chaukhambha Orientalia, Varanasi, Edn. 1st, 1979 pp. 64-65. Formulation ID: RS6/123. Formulation Name: Amra Rasa, written in Sanskrit, including English lanuage summary/translation. Total of 2 pages.
Exhibit 8. Govinda Dasa; Bhaisajya Ratnavali—Edited by Rajeshvaradutta Shastri, translated by Ambikaduttashastri: Chaukhamba Sanskrit Sansthan, Varanasi, Edn. 14th, 2001. [This book contains back references from 1000 B.C. to 18th century] p. 465. Formulation ID: AK/2755. Formulation Name: Savarnakaraneyogah (1), written in Sanskrit, including English language summary/translation. Total of 4 pages.
Exhibit 9. Ziya Al-Din Abdullah lbn Al-Baitar; Al-Jaam'e-li-Mufradaat-al-Advia-wal-Aghzia, vol. IV (13th century AD), Matba Amra, Cairo Egypt, 1874 AD p. 57. Formulation ID: MH2/93. Formulation Name: Karm-e Barri, written in Sanskrit, including English language summary/translation. Total of 4 pages.
Extended European Search Report in the counterpart Application No. 10184946.1, dated Apr. 11, 2011, eleven (11) pages.
Francis, F. J., Food Science and Technology, Second Edition, vol. 1, John Wiley & Sons, Inc., USA, pp. 845-862, 2000.
Galli et al., "Loss of ripening capacity of pawpaw fruit with extended cold storage," J. Agric. Food Chem., 56(22):10683-10688, 2008.
Hewitt, H., et al., "Topical use of papaya in chronic skin ulcer therapy in Jamaica," West Indian Med. J, 2000, pp. 32-33, vol. 49, No. 1.
Hewitt, Hermi, et al., "The Use of Papaya on Pressure Ulcers: A natural alternatives," AJN, Dec. 2002, pp. 73-77, vol. 102, No. 12.
Kenyan Recipe Page, "Siriani," http://nutford.kijabe.org/recipes.html, accessed Feb. 10, 2014.
Keswani, MH., et al., "Histological and bacteriological studies of burn wounds treated with boiled potato peel dressings," Burns, 1990, 16(2): pp. 137-43.
Krell, "Value-added Products from Beekeeping," Food and Agriculture Organization of the United Nations, Food & Agriculture Org., 1996, pp. 294.

Layne, D.R., "Pawpaw," Perdue University Centerior New Crops & Plant Products, 1995, pp. 1-6, http://hort.purdue.edu/newcrop/CropFactSheets/pawpaw.html.
Lucas, T.P., "Papaw Ointment made from the fruit of The Papaw: Treatment from Nature The Papaw Tree," pp. 1-4, http://www.lucaspapaw.com.au/, 2006.
Maybhate, C., "Skin Care for Acne-Prone Skin," Ayurveda Holistic Community, Oct. 2005, pp. 1-5, Women's Health, Beauty Care, http://www.ayurvedahc.com/articlelive/articles/171/1 Skin-Care-for-Acne-prone-Skin.
Nagashima, Tetsuya, et al., "Patents and Formulation of New Skin Cleansing Products," Fragrance Journal, (1984), pp. 8-13, No. 68.
Naldi. L., et al., "Dietary factors and the risk of psoriasis. Results of an Italian case-control study," British Journal of Dermatology, (1996), pp. 101-106, vol. 134.
Narineshingh, Dryer, et al., "Solar Drying Characteristics of Papaya (Carica papaya) Latex," J. Sci. Food Agric., 1988, pp. 175-186, vol. 46, Society of Chemical Industry, Great Britain.
Notice of Reasons for Rejection, Patent Application No. P2004-522026, dated Oct. 20, 2009.
Office Communication issued in U.S. Appl. No. 13/491,829, dated Apr. 2, 2013.
Office Communication issued in U.S. Appl. No. 13/491,829, dated Jan. 3, 2013.
Office Communication issued in U.S. Appl. No. 11/713,206, dated Sep. 9, 2011.
Office Communication issued in U.S. Appl. No. 11/713,206, dated Aug. 4, 2010.
Office Communication issued in U.S. Appl. No. 11/713,206, dated Oct. 30, 2009.
Office Communication issued in U.S. Appl. No. 11/713,206, dated Apr. 14, 2009.
Office Communication issued in U.S. Appl. No. 10/521,380, dated Jul. 23, 2010.
Office Communication issued in U.S. Appl. No. 10/521,380, dated Oct. 16, 2009.
Office Communication issued in U.S. Appl. No. 10/521,380, dated Aug. 14, 2009.
Office Communication issued in U.S. Appl. No. 10/521,380, dated Dec. 10, 2008.
Office Communication issued in U.S. Appl. No. 10/521,380, dated May 28, 2008.
Office Communication issued in U.S. Appl. No. 10/521,380, dated Aug. 10, 2007.
Office Communication issued in U.S. Appl. No. 10/521,380, dated Jul. 25, 2007.
Pawpaw I Caribbean Cooking Recipes, http://www.recipe.dominica-weekly.com/?s=pawpaw%20, Copyright 2005-2014.
Peterson Pawpaws Fact Page; downloaded from www.petersonpawpaws.com web site (2011 ).
Phillipson, J. "New Drugs from Nature—It Could Be Yew," Phytotherapy Research, 13:2-8, 1999.
Revilla et al., "Comparison of several procedures used for the extraction of anthocynains from red grapes," J. Agric. Food Chem., 46:4592-4597, 1998.
Rodrigues, LH, et al., "Comparative study of the effects of cosmetic formulations with our without hydroxy acids on hairless mouse epidermis by histopathologic, morphometric, and stereologic evaluation," J Cosme! Sci., Sep.-Oct. 2002, pp. 269-282, vol. 53, No. 5.
Royal Botanic Gardens, Kew: Information Sheets: Paw, http://www.kew.org/ksheets/pawpaw.html, accessed Feb. 10, 2014.
Schmidt, L., "Way down yonder in the pawpaw patch," lntellingencer Journal, Lancaster, Pa. Oct. 2, 1996, p. C. 1, pp. 1-3 ProQuest.
Sodium Diacetate Chemical Specifications; product information p., Advance In-Organics Company, downloaded from www.advanceinorganics.com/sodium-di-acetatehtm. (2009).
Starley, I.F., et al., "The Treatment of Paediatric Burns Using Topical Papaya," Burns, 1999, pp. 636-639, vol. 25.
Third Party Observations from corresponding Canadian patent application (based on PCT Publication No. W02004/008887). Letter from V.K. Gupta dated Jan. 12, 2011, with comments on Canadian application and the following exhibits. Includes Annex I: Summary

(56) References Cited

OTHER PUBLICATIONS of Traditional Indian Medicine Knowledge. Annex II: Details of Sanskrit, Arabic and Urdu Translations in CIPO. Total of 13 pages.
U.S. Food and Drug Administration, "Approximate PH of Foods and Food Products," http://www.cfsan.fda.gov/~comm/lacf-phs.html, accessed Feb. 7, 2008.
Werner, David, "Home Remedies," Alternate medicine, pp. 1-9, http://www.healthwrights.org/contents/articles/home_remedies.html, accessed Feb. 10, 2014.
Wimalaswansa, "Papaya in the Treatment of Chronic Infected Ulcers," Ceylon Medical Journal, 1981, pp. 129-132, vol. 26.
Winter, R., "A Consumer's Dictionary of Cosmetic Ingredients," Crown Publishers, Inc., 1989, pp. 41, Third Revised Edition.
Author Govt of India Title of publication—Sahastrayoga Page(s) being submitted—06 (p. 04-09) (Ref.p. No. of publication:301 ) Publication Date—1990 Publisher—Central Council for Research in Ayurveda & Siddha Place of Publication—New Delhi, India.†
Author Mahendra Bhaugika Title of publication—Dhanvantarinighantauh Page(s) being submitted—05 (p. 10-14) ( Ref p. No. of publication:223 ) Publication Date—Edn. 3rd, 2002 Publisher—Chaukhambha Orientalia Place of Publication—Varanasi, India.†
Author Kaiyadeva Title of publication—Kaiyadevanighantau Page(s) being submitted—08 (p. 15-22 ) ( Ref.p. No. of publication:64 ) Publication Date—1979 Publisher—Chaukhambha Orientalia Place of Publication—Varanasi, India.†

\* cited by examiner
† cited by third party

PAWPAW AND/OR PEACH DERIVED COMPOSITION

CROSS-REFERENCE TO RELATED APPLICATION

This application is a continuation of co-pending U.S. patent application Ser. No. 13/491,829, filed on Jun. 8, 2012, which is a continuation of U.S. patent application Ser. No. 11/713,206, filed on Mar. 1, 2007, now U.S. Pat. No. 8,216,615, which is a continuation of U.S. patent application Ser. No. 10/521,380, filed on Jan. 6, 2006, now abandoned, which was filed under 35 U.S.C. 371 as a National Stage of International Application No. PCT/AU2003/000931, with an International filing date of Jul. 22, 2003, and which claims the benefit from Australian Patent Application No. 2002950308, filed on Jul. 23, 2002, the entire content of each of which is hereby incorporated by reference in its entirety.

TECHNICAL FIELD

The present invention relates to a composition derived from fruit and/or vegetables and which is suitable for topical application. In particular the present invention relates to a fruit and/or vegetable derived composition suitable for topical application to the skin to treat and prevent dermatological disorders and to provide relief for muscular and joint pain. The present invention also relates to a process for preparing a fruit and/or vegetable derived composition suitable for at least the treatment and prophylaxis of dermatological and cosmetic disorders.

BACKGROUND

In a large number of cases, topical products such as soaps, cosmetics and pharmaceuticals contain chemicals or other ingredients such as preservatives, solvents and fragrances, which may produce irritation including various inflammation symptoms or signs when applied to the skin. The present invention is directed in part to compositions and methods for inhibiting the irritation associated with such topical products. The frequency and nature of skin irritation induced by such topical products can range from mild to severe and includes such symptoms as itching, stinging, redness, burning and swelling. The symptoms may be severe in people who have sensitive skin. Whatever is the cause of such irritation, many products are presented as 'hypoallergenic' with minimal irritant potential, yet do not achieve reduced irritancy due to their formulation or constituent ingredients.

Further, the skin is subject to stress and deterioration through dermatological disorders, environmental effects and exposure as well as through the ageing process.

Skin cells are generally more exposed to environmentally generated injuries than internal body cells. Of particular concern are cancer causing chemicals and free oxygen radicals.

Topical application and/or oral ingestion of Vitamins A (beta-carotene, CAS 7235407), C (ascorbic acid, CAS 50817) and E (alpha-tocopherol, CAS 59=029), has been shown to provide protection against these chemicals, including free radicals. Citric acid, malic acid and tartaric acid are the prominent acids in fruits and to some degree vegetables. They are usually referred to as alpha-beta-hydroxy acids. Other similar ingredients are alpha hydroxy acids like glycolic acid or lactic acid.

The exfoliating effects of such acids depend very much on the concentration of the acids and the pH. Therefore, it can be said that the more acidic and the higher the concentration, the stronger the effect. However this is also associated with an increase in side effects. At higher concentrations applied over longer periods, the skin reacts; becoming red, swollen, sensitive and blisters may form. Rashes and itching may occur. Exposure to the sunlight will exacerbate such reactions.

Since 1989 the US Food and Drug Administration (FDA) has received more than 100 reports of adverse reactions in people using alpha hydroxy acid products. Based on past experience with complaints the FDA extrapolates from these 100 complaints that there have been approximately 10,000 adverse reactions. Products containing alpha hydroxy acids will be either regulated as cosmetics, or drugs or both depending on their intended use. In particular, pharmaceutical effects after penetration of the skin barrier, like increasing cell turnover rate and decreasing thickness of the outer skin are of concern to the FDA. These effects depend on the acidity, the concentration of the acids, and the cosmetic carrier.

Further, many fruit based products topically applied to the skin have a pH in the acidic range and can cause irritation to the skin.

There therefore exists a need for a topically applied fruit and/or vegetable derived composition and process for preparing the same which minimises or prevents irritation of the skin caused by topical application but which is still efficacious in treating dermatological disorders and cosmetic applications.

OBJECT OF THE INVENTION

The present invention attempts to overcome at least in part some of the aforementioned disadvantages by providing a new fruit and/or vegetable derived composition which can be safely applied without resulting irritation and process for preparing the same.

It is the object of the present invention to overcome or substantially ameliorate at least one of the above disadvantages by provision of an efficacious composition derived from natural ingredients which reduces or minimises skin irritation while treating and/or preventing dermatological and cosmetic disorders.

SUMMARY OF THE INVENTION

In accordance with a first aspect of the present invention, there is provided a process for making a composition comprising the steps of:

a) heating a fruit and/or vegetable pulp to up to a temperature in the range of about 40° C. to 100° C.; and b) mixing between 1 and 40% w/w of a mild base with the heated fruit and/or vegetable pulp.

In accordance with a second aspect of the present invention, there is provided a composition prepared by the process of the first aspect of the present invention defined above.

In accordance with a third aspect of the present invention, there is provided a composition which is suitable for topical application comprising at least one fruit and/or vegetable derived pulp and a mild base, said composition having a pH in the range of about 7.5 to 9.5.

In accordance with a fourth aspect of the present invention, there is provided a method of treating or preventing dermatological and epidermal disorders comprising the topical application of an effective amount of a composition of the second or third aspects of the present invention as defined above to a mammal in need of such treatment or prophylaxis.

In accordance with a fifth aspect of the present invention, there is provided a method of treating pain associated with arthritis, gout and other muscular and joint related aches and pains comprising the topical application of an effective amount of a composition of the second or third aspects of the present invention defined above to a mammal in need of such treatment.

In accordance with a sixth aspect of the present invention there is provided a process for making a composition suitable for topical application comprising the steps of:

a) heating at least one fruit and/or vegetable pulp to up to a temperature in the range of about 40° C. to 100° C.;

b) mixing between 1 and 40% w/w of a mild base with the heated fruit and/or vegetable pulp; and c) filtering the mixture to obtain the composition.

In accordance with a seventh aspect of the present invention there is provided a process for making a composition suitable for topical application comprising the steps of:

a) heating at least one fruit and/or vegetable pulp to up to a temperature in the range of about 40° C. to 100° C.;

b) mixing between 1 and 40% w/w of a mild base with the heated fruit and/or vegetable pulp;

c) beating the resulting mixture;

d) freezing the beaten mixture;

e) thawing and then filtering the mixture to obtain the composition.

DETAILED DESCRIPTION

Dermatological disorders such as psoriasis, eczema, acne, wrinkles, sagging, aged and dry skin as well as damaged and sensitive skin can be treated by topical application of a composition including at least one fruit and/or vegetable-derived pulp and a mild base on an affected area of skin.

The pulp may be derived from an inner fleshy part of the fruit or vegetable, or alternatively, from a mixture of the skin and an outer fleshy part of the fruit or vegetable. In some cases, and depending on the type of fruit or vegetable, the whole fruit or vegetable may be pulped. In other cases, and again depending on the type of fruit or vegetable, just the skin of the fruit or vegetable may be pulped.

Particularly in respect of fresh fruit, in order to ensure consistent quality, vitamin C concentration can be measured to indicate the quality of the fruit and therefore of the raw material to be pulped.

Typically, the fruit or vegetable may be selected from a group including peaches, pawpaw, mango, lime, mandarin, grapes, rockmelon, oranges, passion fruit, lemon, plums, pineapple, pear, apple, tomato, avocado, potato, capsicum, pumpkin, carrots, lettuce, cucumber, cabbage and beetroot, apricots, melons including watermelon and rockmelon, grapefruit, berries including strawberries, blueberries, mulberries and raspberries, and bananas.

Typically, the fruit or vegetable can be fresh, frozen, tinned or bottled. Most typically, the fruit or vegetable is fresh and raw. The tinned or bottled fruit is typically solely natural without any preservatives being present.

Typically, the fruit or vegetable has the skin removed prior to pulping. It is also typical that the fruit and/or vegetable skin can be pulped separately. For example, pawpaw flesh can be pulped separately and utilised in the process of the present invention, and pawpaw skin can also be pulped separately. It is also typical that mango flesh can be pulped separately to mango skin. Typically, lime skin is pulped separately to lime flesh and it is also typical that mandarin skin is pulped separately to mandarin flesh.

More typically, fruit is utilised, particularly fruit which is slightly acidic such as mandarin, tomato, oranges, pawpaw and lime.

Most typically, the fruit which is used is selected from the group consisting of pawpaw, tomato and peaches.

In order to maximise activity of the composition of the present invention, a small amount of lime flesh can be added to the fruit or vegetable at the time of pulping. This is preferred where solely vegetables, for example, pumpkin, are being pulped.

In one embodiment a mixture of different fruits can be pulped together. For example, pawpaw flesh and mango flesh have been jointly pulped together. Alternatively, a mixture of different fruits and vegetables can be pulped together. For example, pawpaw flesh and tomato flesh have been pulped together and pawpaw flesh and peach and tomato flesh have also been pulped together. Also typically, a mixture of different vegetables can be pulped together. For example, a mixture of beetroot and potato flesh has been pulped together. Alternatively, different fruits and vegetables are pulped separately. It is preferred that each separate fruit or vegetable is pulped separately ie solely mango flesh is pulped or solely tomato flesh is pulped and these separate pulps are typically added together prior to the initial heating step. More typically, the separate pulps are processed separately according to the present invention, namely heated and the mild base is added and the resulting compositions are added together either as raw product or together in a formulation. It is also typical that the separate pulps are processed and maintained and utilised separately.

As an example of separate pulpings, pawpaw is pulped and processed according to the present invention separately to mango and also separately to peach and the resulting pawpaw derived, mango derived and peach derived extracts can be either formulated together in a final cream or lotion to enhance the beneficial properties of each of these compositions when used separately.

It is also very typical that the active filtrates resulting from the processing of separate individual fruit or vegetable pulps are mixed after filtering.

As used herein the phrase "fruit and/or vegetable pulp" means that the fruit and/or vegetable flesh has been macerated to a pulp in the form of a viscous liquid or pureed or otherwise processed to result in a pulp. Typically a food processor or hand mixer or other mechanical apparatus is used to pulp the fruit and/or vegetable flesh. As stated above in some instances, a mixture of fruit flesh and skin and/or vegetable flesh and skin is processed to a pulp in the form of a viscous liquid. Where a fruit or vegetable is used which contains a stone or "pip", the stone or pip is removed prior to pulping.

The composition of the present invention may be prepared by first pulping the selected fruit and/or vegetable to a viscous liquid pulp, then heating the fruit and/or vegetable pulp to a temperature above about 40° C., typically to a temperature in the range of about 40° C. to about 80° C., more typically to a temperature in the range of about 45° C. to 75° C. Even more typically, the pulp is heated to a temperature in the range of about 50° C. to 70° C., more typically to a temperature in the range of about 50° C. to 60° C. Most typically, the pulp is heated to a temperature of about 55° C.

Typically the pulp may be heated by any means such as a microwave, or an electric or gas stove, or by use of a double boiler in a stove. Typically, the pulp is stirred during the heating process and the temperature of the pulp periodically taken until about 55° C. is reached.

To the heated pulp is then added a mild base in an amount of between 1 and 40% w/w of the pulp. Typically, the base is a mild base. The term "mild base" as used herein is understood to define a base having a pKa of less than about 1. Typically, the mild base is selected from the group consisting of $CO_3^{2-}$, $CN-$, $NH_3$, $HS^-$, $HCO_3^-$, $CH_3CO_2^-$, $NO_2^-$, $F-$, $H_2PO_4^-$, $SO_4^{2-}$, $NO_3-$, $Cl-$, $Br-$, $I-$, $HSO_4^-$ and $ClO_4^-$. More typically, the mild base is a water-soluble alkali metal salt of a base selected from the above list. Even more typically, the mild base a water-soluble alkali metal bicarbonate or carbonate salt, in particular sodium bicarbonate, sodium carbonate, potassium bicarbonate, and potassium carbonate. Most typically, the mild base is sodium bicarbonate.

Typically, the mild base is added to the pulp with vigorous stirring or agitation. It is typical that the heated pulp is removed from the heat source during the addition of the mild base with stirring.

Typically the amount of base which is added is between about 1 and 40% w/w of the pulp. More typically, the amount of base which is added is in the order of about 1 to 35% w/w, and even more typically about 1 to 30% w/w. Also more typically, the amount of mild base which is added is in the order of between about 1 to 25% w/w, and even more typically 1 to 20% w/w. More typically, the amount of mild base which is added is in the order of about 2 to 15% w/w, in particular 3 to 14% w/w or 4 to 13% w/w. Most typically, the amount of mild base which is added is in the order of between about 5 to 10% w/w, most typically 10% w/w. Accordingly, for example, 30 grams of sodium bicarbonate will be added to 300 grams of fruit pulp as a 10% w/w.

Typically, the mild base is added with agitation to the pulped fruit and/or vegetable until effervescence ceases. Following this step, it is typical that the resulting mixture is thoroughly mixed, more typically beaten until the texture is that of a flowing cream. Typically this beating/mixing step takes about 10 to 80 seconds, more typically about 20 to 60 seconds, even more typically about 20 to 40 seconds. The beating is typically undertaken to aerate the mixture and improve the consistency of the final product. This beating/mixing step is preferred to be performed after the effervescence following addition of the mild base ceases. The resulting beaten mixture has the consistency of smooth, flowing, fairly viscous liquid as it is essentially a thick fruit whip. If the mixture following addition of the base is not mixed, once the effervescence following addition of the base ceases, the mixture is very much like a type of fruit cappuccino with froth remaining on the top of the mixing bowl. As it is typical that the mixture is then beaten, the consistency is smooth and even throughout with no froth.

In the case of the composition formed from the inner flesh or the outer flesh and skin of the mango, however, there is no requirement to filter the composition before it is applied to the skin.

It is typical that after the fruit and/or vegetable pulp is beaten to a smooth cream that the mixture is then frozen. Typically, following freezing, the frozen mixture is then thawed. If the freezing step is omitted, then the composition can become of gellike consistency. Typically, the thawed mixture or the mixture obtained after the addition of the mild base (which is not frozen), is filtered. Typically, the filtration of the thawed frozen mixture, or of the mixture obtained following addition of the base, is by way of allowing the mixture to filter through calico or other similar fabric for 12 to 24 hours. Other filtration methods/devices can also typically be utilised. As stated above, it is not essential that the mixture be frozen or filtered and therefore it is also typical that the mixture obtained after addition of the mild base is an active composition which can be utilised in the methods of the present invention. It is, however, preferred that the mixture be frozen, thawed then filtered. Typically, the thawing occurs simply at room temperature. The filtrate derived is an active composition. It can then be used directly as the active composition in accordance with the methods of the present invention or otherwise formulated as outlined below. If formulated as outlined below, it is then utilised in the same methods as the present invention set out below.

Typically, if the mixture post the addition of the base and once the effervescence has ceased is beaten, frozen, thawed then filtered, the filtrate is a liquid which may be translucent or somewhat transparent and is generally coloured the same colour as the flesh of the original fruit and/or vegetable pulp. Typically, when the frothy mixture resulting after the effervescence following addition of the mild base has ceased, is beaten then filtered, the filtrate may become of gellike consistency within several hours.

Typically, the resulting active filtrate composition has a pH in the range of about 7.5 to about 9.5. More typically, the pH of the resulting filtrate composition is in the range of about 7.9 to 9.2. More typically, the pH of the active filtrate composition is between about 8.2 and 9.5. For example, pulped mango flesh which is processed in accordance with the first aspect of the present invention which is then frozen, thawed and filtered has a resulting active filtrate which pH is about 9. The pH of the active composition resulting after the processing of pawpaw is about 9.2. It is also typical that the frothy, cappuccinolike fruit whip mixture resulting after the addition of the mild base and effervescence has ceased has a pH in the range of about 7.5 to about 9.5. For example, post pulping, peach flesh pulp has a pH of about 4, however the pH of the peach composition following addition of 10% w/w $NaHCO_3$, is about 8.5. The pH is measured typically by a pH meter throughout the manufacturing process.

The amount of mild base which is to be added can be calculated according to the acidity of each batch of fruit and/or vegetable pulp and the end pH in the range of about 7.5 to about 9.5 that is desired.

Typically, preservative can be added to the resulting filtrate composition in order to ensure its longevity. Such preservatives can include conventional natural preservatives, typically grapefruit seed extract.

The composition of the present invention, in neat form, may be directly topically applied to an area of skin in need of treatment. Typically, the resulting active filtrate composition is applied directly as the filtrate without dilution, or alternatively, the filtrate can be slightly diluted with water before being applied topically. Alternatively, the active composition resulting after the addition of the base and cessation of frothing, which has not been frozen, thawed and filtered, ie the thick, viscous "fruit whip" like composition can also be applied directly to the skin or diluted and then applied. Alternatively, the compositions of the present invention (which are defined to include the active filtrate composition as well as the active composition resulting after addition of a mild base to pulp) can be formulated and topically applied as a soap, gel, cream, lotion, ointment or the like by the addition of pharmaceutically acceptable carriers or excipients. Preferred carriers include deionised water, vegetable or mineral oils, white petrolatum, branched chain fats or oils, animal fats and high molecular weight alcohol. Emulsifiers, stabilisers and antioxidants may also be included as well as colouring agents and essential oils to impart fragrance.

It is typical that the compositions of the present invention can be formulated as a lotion or tonic, where they are either applied directly, or diluted with water and then applied. The compositions can also be formulated as creams or ointments. In such formulations the active composition may be added in an amount of 10% to 60% w/w of base moisturiser cream and mixed in with the base cream. For example, sorbolene cream or other moisturisers can have compositions of the present invention added to them in an amount of 10% to 60% w/w. Alternatively, macadamia oil, jojoba oil, almond oil or other nut and seed oils may be have the active composition of the present invention added to them in an amount of 10% to 60% w/w.

Creams, lotions, tonics and other formulations can be prepared using one or more actives. For example, base moisturiser can be taken and 5% w/w of composition "A" from Example 1 and 5% w/w of composition from "M" (from Example 3) can be added to the moisturiser. It is also typical that two or three or even more active compositions can be added to a single formulation, or can be mixed together directly without the need for excipients or carriers.

Other topical products in which the compositions of the present invention can be formulated include skin care products such as creams, gels, pastes, emulsions, salves, exfoliants, cleansers, toners, sprays, masques and peels, sunscreens, lipbalms, lipsticks, depilatories, facial and body soaps and the like.

Suitable topical vehicles for use with the formulations of the present invention are well known in the cosmetic and pharmaceutical areas and include water, lipid bases materials including oils and fats, soaps, surfactants, emollients, skin conditioning agents and emulsifying agents. Examples of these vehicles are described Martindale The Extra Pharmacopoeia (Pharmaceutical Press). Clearly, the choice of a suitable vehicle depends on the mode of delivery of the formulation. The active composition is generally incorporated in the dermatologically/cosmetically acceptable vehicle/carrier in a conventional manner well known in the cosmetic and pharmaceutical arts.

Topical application of an efficacious amount of the fruit and/or vegetable derived product of the present invention to an area of skin in need of treatment affords fast and effective relief from the symptoms of various dermatological disorders including psoriasis, eczema, dry skin, wrinkles, and acne. The area of treated skin takes on an improved skin tone and appears smoother and more taut. Dry and flaking skin is exfoliated from the surface of the skin, and inflamed and reddened skin is soothed.

Typically, a composition of the present invention is topically applied to an animal, preferably a human, for the treatment or prophylaxis of all epidermal disorders including psoriasis, eczema, insect bites, general epidermal irritation and redness including rosacea and itchiness, alopecia, circulatory disorders affecting the epidermis, sunburn, windburn and first, second and third degree burns, healing of sores, wounds and skin infections, skin cancers including sunspots, skin melanomas, and also alleviates some gum diseases and mouth ulcers and other gum and mouth dermatological disorders. Also typically, the composition of the present invention can be topically applied to arthritic joints to alleviate pain and swelling associated with all forms of arthritis as well as general joint and muscle aches and pains.

Also typically, the composition of the present invention is applied as a general pain reliever. It can also be typically applied to prevent sunburn.

It is also typical that the composition of the present invention is applied to the treatment of gout. Typically, a composition derived from peach flesh pulp is best used to treat eczema, and it is also typical that a composition derived from mango pulp can be used. It is also typical that composition derived from pulped potato flesh can be used a skin whitener. Typically a composition being a mixture of active compositions derived from pawpaw flesh (A) and peach flesh (M) can be used to reduce swelling and to minimise pain associated with rheumatoid arthritis and gout and to improve blood circulation.

Also typically, the composition of the present invention can be topically applied, particularly to the face and hands and neck to achieve an enhanced cosmetic benefit. More typically, the composition of the present invention can be applied topically to the epidermis as an exfoliant, as an effective astringent or antibacterial, as well as an excellent skin cleanser and freshener. Typically, it reduces wrinkles and reduces effects of ageing on the epidermis. A general improvement in clarity, skin texture and appearance is observed after application of a composition of the present invention.

Typically, one or more pure compositions of the present invention is topically applied to the area of skin in need of treatment, allowed to penetrate the skin for a period of up to typically 30 to 90 minutes, more typically 60 minutes and then the composition is removed from the skin by rinsing with water. If more than one composition is being applied the first coat is allowed to dry before the next coat is applied. For example it is typical that a lotion comprising pure liquid active filtrate A is applied first to the face, this is then allowed to dry before a coat of pure liquid E is applied. Alternatively 2 coats of each can be applied. The dried coats are washed off after about one hour. This can be repeated typically once every two three days, or even every day depending on the disorder being treated and the sensitivity of the skin.

Also typically, a formulation containing a composition of the present invention, such as a cream, oil or ointment is simply topically applied to the appropriate area and allowed to remain.

Accordingly, it is typical that the topical compositions of the present invention can be in the form of a 'washoff' product such as a masque or lotion or gel, or can be formulated as a product to be left on such as a cream or ointment.

While not wishing to be bound by theory, it is noted that the addition of a mild base under raised temperature conditions, chemically reacts with the acids (eg citric acid, tartaric acid, malic acid) and other components in the pulped fruit and/or vegetable material to form a number of chemical products including salts. The mild base is acting as a buffer agent to increase the pH (ie reduce the acidity) of the product.

The present inventive method of extraction from the fruit and/or vegetable pulp provides a new and useful composition.

The pulped fruit and/or vegetable material will typically contain carbohydrates (sugars) particularly glucose, fructose, maltose and sucrose.

The pulped material will also contain some nitrogen containing substances such as proteins (amino acids), amides, amine nitrates depending on the source of the pulp. Vegetables contain between about 15.5% while in fruit nitrogen containing substances are <1%. The proteins in the pulped mixture may be destroyed when the heating occurs above 50° C. The heating step in the present process may therefore destroy microorganisms and may to some extent affect the activity of proteins present (particularly enzymes). This heating step therefore improves the storage stability of the pulped material and will determine which components remain in the active composition. Enzyme activity in the active composition is not expected to be totally deactivated by the process, however some enzymes may be more affected than others depending on their susceptibility to changes in pH and temperature.

Pulped fruit material will contain alpha-beta hydroxy acids such as citric acid, malic acid and tartaric acid as mentioned above. Alpha hydroxy acids may also be present in the fruit/vegetable pulp. Malic acid, citric acid and tartaric acid are not toxic and at pH of the present invention should not cause skin or ocular irritability.

As the pH of the pulped material is low it is anticipated that no microorganisms (which could affect the fruit or vegetable material eg by fermentation) are present. In any event, heating of the pulped material before addition of a base minimises the likelihood of viable microorganisms being retained when the pH is increased. Conditions of processing are however, kept as clear and sterile as possible to minimise the presence of microorganisms/bacteria.

The present invention will now be further described with reference to the following examples.

Modifications, changes and variations as would be apparent to a skilled addressee are deemed to be within the scope of the present invention-particularly with regard to specific exemplary components and to the specific ranges of the components.

EXAMPLES

Example 1(A)

1. Take normal fresh pawpaw, not unripened or overripe.
  (a) Remove skin and outer layer of hard flesh.
  (b) Remove seeds.
2. Take 300 gm of pawpaw flesh and place in Pyrex bowl.
3. Pulp pawpaw flesh with a hand-mixer.
4. Place pulped pawpaw flesh into the top pan of a stainless steel double-boiler.
5. Fill the bottom pan of the double-boiler with water to about two-thirds full.
6. Place bottom pan of the double-boiler on stove or hot plate and bring to the boil.
7. Place the top pan containing the pulped pawpaw flesh on top of the bottom pan.
8. Continue heating the bottom pan whilst manually stirring the pulped pawpaw is flesh in the top pan using a wooden spoon until the temperature of the pulped pawpaw flesh reaches about 55.degree. Celsius.
9. Preheat 1 liter Pyrex bowl to about 55° Celsius.
10. Transfer heated pulped pawpaw flesh to heated Pyrex bowl.
11. Add 30 gm of sodium bicarbonate (as purchased in a supermarket) to heated pulped pawpaw flesh.
12. Stir heated pulped pawpaw flesh vigorously with a wooden spoon until effervescence ceases.
13. Beat heated pulped pawpaw flesh vigorously using an electric mixer until texture is that of a smooth cream. This takes 20 to 40 seconds.
14. Pour the heated pulped pawpaw flesh into a container.
15. Put lid on container.
16. Place container in deepfreeze.
17. After the contents of the container have frozen remove container from deepfreeze and allow to thaw.
18. Allow thawed liquor to filter through calico for 12 to 24 hours and collect in Pyrex bowl.
19. The collected liquor (filtrate) is the active raw composition demonstrating efficacy and producing the beneficial effects.

Formulation of Raw Product

1. Use raw product as a lotion or tonic.
2. Add raw product to a base lotion such as sorbolene or other moisturiser to produce a viscous lotion.
3. Add raw product to a natural oil such as macadamia that has been heated and then allowed to cool to 45° Celsius thereby creating a cream.
4. Add raw product to a mixture of lye and oils used in making soap before saponification takes place thereby making a soap.

Beneficial Effects

1. General skin care.
  a) Excellent exfoliant
  b) Extremely effective astringent
  c) Excellent skin cleanser and freshener
  d) Gives skin a healthy look and feel
  e) Removes wrinkles
  f) Generally makes the skin on face look and feel fresher, tighter and younger
2. Heals cuts and wounds.
3. Relieves a large variety of skin afflictions, including skin cancers.
4. Takes the sting out of insect bites.
5. In some cases, restores hair growth.
6. Relieves sores in gums and alleviates some gum diseases.
7. Can be combined with other products prepared according to the process of the present invention and will demonstrate synergistic effects in respect of those products. It has been noted that with most of the other compositions of the present invention, the resulting composition of Example 1(A) enhances the effectiveness of those other compositions.

Notes in Respect of Example 1(A)

1. The heating step can be effected in a microwave rather than a double-boiler.
2. The optimum temperature is 55° C. and the preferred temperature range is 50° C. to 60° C. Product with beneficial properties can be created if the temperature is between 40° C. and 100° C.
3. The proportion of sodium bicarbonate can be varied from 1% to 40% of the pulped flesh by weight. The lower proportion of sodium bicarbonate is more suitable for persons with extremely sensitive skin. As the proportion of sodium bicarbonate increases the raw product becomes progressively more likely to burn the skin.
4. The pH of the final product when the weight of sodium bicarbonate is 10% of the weight of the pulped pawpaw flesh is approximately 8.
5. The freezing step may be omitted, but in some cases, the product formed from adding sodium bicarbonate to the heated pulped flesh becomes gellike and the filtration of the liquor is more difficult.

Example 2(H)

1. Take normal fresh tomato, not unripened or overripe.
2. Take 300 gm of tomato and place in Pyrex bowl.
3. Pulp tomato with a hand-mixer.
4. Place pulped tomato into the top pan of a stainless steel double-boiler.
5. Fill the bottom pan of the double-boiler with water to about two-thirds full.
6. Place bottom pan of the double-boiler on stove or hot plate and bring to the boil.
7. Place the top pan containing the pulped tomato on top of the bottom pan.
8. Continue heating the bottom pan whilst manually stirring the pulped tomato in the top pan using a wooden spoon until the temperature of the pulped tomato reaches about 55° Celsius.
9. Preheat 1 liter Pyrex bowl to about 55° Celsius.
10. Transfer heated pulped tomato to heated Pyrex bowl.
11. Add 30 gm of sodium bicarbonate (as purchased in a supermarket) to heated pulped tomato.
12. Stir heated pulped tomato vigorously with a wooden spoon until effervescence ceases.
13. Beat heated pulped tomato vigorously using an electric mixer until texture is that of a smooth cream. This takes about 20 to 40 seconds.
14. Strain the product of the heated tomato pulp and the sodium bicarbonate using a stainless steel trainer with apertures of 0.8 mm. collecting the liquor in a Pyrex bowl.
15. The collected liquor (filtrate) is the active raw composition demonstrating efficacy and producing the beneficial effects.

Formulation of Raw Product

1. Use raw product as a lotion or tonic.
2. Add raw product to a base lotion such as sorbolene or other moisturiser to produce a viscous lotion.
3. Add raw product to a natural oil such as macadamia that has been heated and then allowed to cool to 45° C. thereby creating a cream.
4. Add raw product to a mixture of lye and oils used in making soap before saponification takes place thereby making a soap.

Beneficial Effects

1. General skin care.
2. Alleviates a number of skin afflictions.
3. Effectively treats most types of psoriasis.
4. Takes the itch out of irritated skin.
5. Takes the sting out of insect bites.
6. Can be combined with other products of the process of the present invention to demonstrate a synergistic beneficial effect.

Notes

1. The heating step can be effected in a microwave rather than a double-boiler.
2. The optimum temperature is 55° C. and the preferred temperature range is 50° C. to 60° C. Product with beneficial properties can be created if the temperature is between 40° C. and 100° C.
3. The proportion of sodium bicarbonate can be varied from 1% to 40% of the pulped flesh by weight. The lower proportion of sodium bicarbonate is more suitable for persons with extremely sensitive skin. As the proportion of sodium bicarbonate increases the raw product becomes progressively more likely to burn the skin.
4. The pH of the final product when the weight of sodium bicarbonate is 10% of the weight of the pulped tomato flesh is approximately 8.

Example 3(M)

1. Take normal fresh peaches, not unripened or overripe.
    a) Skin peaches.
    b) Remove stones.
2. Take 300 gm of peach flesh and place in Pyrex bowl.
3. Pulp peach flesh with a hand-mixer.
4. Place pulped peach flesh into the top pan of a stainless steel double-boiler.
5. Fill the bottom pan of the double-boiler with water to about two-thirds full.
6. Place bottom pan of the double-boiler on stove or hot plate and bring to the boil.
7. Place the top pan containing the pulped peach flesh on top of the bottom pan.
8. Continue heating the bottom pan whilst manually stirring the pulped peach flesh in the top pan using a wooden spoon until the temperature of the pulped peach flesh reaches about 55° C.
9. Preheat 1 liter Pyrex bowl to about 55° C.
10. Transfer heated pulped peach flesh to heated Pyrex bowl.
11. Add 30 gm of sodium bicarbonate (as purchased in a supermarket) to heated pulped peach flesh.
12. Stir heated pulped peach flesh vigorously with a wooden spoon until effervescence ceases.
13. Beat heated pulped peach flesh vigorously using an electric mixer until texture is that of a smooth cream. This takes about 20 to 40 seconds.
14. Pour the heated pulped pawpaw flesh into a container.
15. Put lid on container.
16. Place container in deepfreeze.
17. After the contents of the container have frozen remove container from deep freeze and allow to thaw.
18. Allow thawed liquor to filter through calico for 12 to 24 hours and collect in Pyrex bowl.
19. The collected liquor (filtrate) is the active raw composition demonstrating efficacy and producing the beneficial effects.

Formulation of Raw Product

1. Use raw product as a lotion or tonic.
2. Add raw product to a base lotion such as sorbolene or other moisturiser to produce a viscous lotion.
3. Add raw product to a natural oil such as macadamia that has been heated and then allowed to cool to 45.degree. C. thereby creating a cream.
4. Add raw product to a mixture of lye and oils used in making soap before saponification takes place thereby making a soap.

Beneficial Effects

1. General skin care.
2. Heals burns that have already developed.
3. Prevents burns from developing after the skin has been "burnt".
4. Gives instant relief from sunburn.
5. Prevents sunburn if applied before going out in the sun.

6. Alleviates the affects on the skin of eczema and many types of psoriasis.

7. Alleviates acne.

8. Heals sores and wounds.

9. Relieves many types of pain.

10. This product can be combined with other products prepared according to the process of the present invention to demonstrate enhanced beneficial effects.

In combination with the product of Example 1, the raw product created from the inner flesh of pawpaw, the following effects have been noted:

1. Gangrenous flesh can be restored to normal healthy skin and flesh.

2. Burn prevention and healing, including relief from the pain associated with the burn, is enhanced.

3. Most types of swelling are reduced, in some cases instantaneously.

4. In the case of treatment of gout and arthritis and other muscular and joint pain and aches, the swelling and pain was reduced almost instantaneously.

5. Blood circulation is improved.

Notes

1. Tinned peaches can be used in place of natural peaches. The entire contents of the can, including the liquor is used.

General Notes

1. The heating step can be effected in a microwave rather than a double-boiler.

2. The optimum temperature is 55° C. and the preferred temperature range is 50° C. to 60° C. Product with beneficial properties can be created if the temperature is between 40° C. and 100° C.

3. The proportion of sodium bicarbonate can be varied from 1% to 40% of the pulped peach flesh by weight. The lower proportion of sodium bicarbonate is more suitable for persons with extremely sensitive skin. As the proportion of sodium bicarbonate increases the raw product becomes progressively more likely to burn the skin.

4. The pH of the final product when the weight of sodium bicarbonate is 10% of the weight of the pulped peach flesh is approximately 8.58.7.

5. The freezing step may be omitted, but in some cases, the product formed from adding sodium bicarbonate to the heated pulped flesh becomes gellike and the filtration of the liquor is more difficult.

Example 4

The firm flesh of a tomato is pulped and heated to a temperature of 55° C. To the heated pulp is added sodium bicarbonate in an amount of about 10% w/w of the total composition. The mixture is thoroughly combined, then frozen. The frozen mixture is thawed, repulped and filtered to afford a filtrate.

The inner flesh of a pawpaw, the outer flesh and skin of the pawpaw, and the inner flesh of a mango, are each treated as described above, except that the composition derived from the inner flesh of the mango is not filtered.

About 50 g of the filtrate resulting from the pulped tomato, and about 30 g each of the filtrates resulting from the inner flesh of the pawpaw, the outer flesh and skin of the pawpaw, and the inner flesh of the mango are combined and mixed thoroughly.

The combined filtrates are applied to an area of skin afflicted with psoriasis. The combined filtrates are allowed to dry on the skin for a period of about 30 minutes and then rinsed from the treated skin with water.

The treatment is repeated after 24 hours.

The symptoms of psoriasis on the treated skin are completely relieved, and there has been no reappearance of the symptoms or the disease.

Example 5

Pawpaw skin is processed exactly according to Example 1 to produce composition B.

Example 6

Mango flesh is processed exactly according to Example 1 to produce composition C.

Example 7

Mango skin is processed exactly according to Example 1 to produce composition D.

Example 8

Lime flesh is processed exactly according to Example 1 to produce composition E.

Example 9

Lime skin is processed exactly according to Example 1 to produce composition E'.

Example 10

Mandarin flesh is processed exactly according to Example 1 to produce composition F.

Example 11

Grapes are processed exactly according to Example 1 to produce composition G.

Example 12

Pineapple is processed exactly according to Example 1 to produce composition I.

Example 13

Avocado flesh is processed exactly according to Example 1 to produce composition J.

Example 14

Apples are processed exactly according to Example 1 to produce composition K.

Example 15

Watermelon flesh is processed exactly according to Example 1 to produce composition L.

Example 16

Grapefruit flesh is processed exactly according to Example 1 to produce composition N.

Example 17

Apricot flesh is processed exactly according to Example 1 to produce composition O.

Example 18

Skin Complaints

The patient, who is a retired 68 year old Australian male, has no skin complaints. He has suffered from rheumatoid arthritis in his hands and knees for about 12 years.

Previous Medication and Results

The patient was diagnosed with a rheumatoid factor through blood tests when he went to see his doctor after beginning to experience pain and stiffness in his wrists and knees. The patient began suffering from the disease at about the same time that his wife contracted Ross River fever and then PMR.

It was explained to the patient by his doctor that the cause of the rheumatoid arthritis is that the immune system begins to go haywire, and that the joints are attacked, causing the pain and stiffness that he was experiencing. His doctor explained that there was no cure, and that the most that he could expect was medication that would control the pain.

The patient was prescribed Voltaren tablets as an anti-inflammatory. Until recently, he has taken two Voltaren tablets each day for the last 12 years or so. For the last five years, The patient has also taken the drug Methotrexate on a weekly basis as a painkiller. However, Methotrexate can have dangerous side effects, and the patient needs to have a monthly blood test to ensure that the use of the drug is not causing any damage to his liver or kidneys.

Some time after commencing using Voltaren tablets, the patient also began using Voltaren cream, which is available OTC, when the pain was intense. It was his doctor who recommended the Voltaren cream; however, his doctor also recommended that the patient not become too reliant on the Voltaren cream because of its expense ($27 for a small tube) and the amount that needed to be applied. The patient found that the Voltaren cream gave him effective relief from the pain, and this relief would last for some hours. The patient estimates that on average he would use Voltaren cream 3 or 4 times per week.

On one occasion, his doctor recommended another cream called Naprosene. The patient found this had no beneficial effect at all, but in fact caused an adverse affect. He experienced what he calls "water blisters" on the areas where he applied the Naprosene.

Products Supplied

The patient was provided with a cream containing the product produced by Example 1.

Results

The patient has found that the cream supplied is far more effective than the Voltaren cream. On the first occasion that the patient used the cream prepared according to the present invention, he was experiencing acute pain in both hands and one of his knees. The patient smothered the cream prepared according to the present invention on both hands and rubbed it into the finger joints during the evening, and applied some more cream before going to bed. The pain had completely disappeared in his right hand and was only very slight in his left hand when he awoke the next morning, and the swelling and stiffness were significantly reduced.

The patient has had to give up golf because of his rheumatoid arthritis, but still plays bowls regularly even though he knows that this will cause his wrists and knees to become more painful. The patient knew from experience that the best way of controlling the resultant pain was to use the Voltaren cream after a morning playing bowls, and the subsequent swim and shower that is part of his routine. He would smear the Voltaren cream on his wrists and knees after the shower and then again at night before going to bed. If he did not do this he knew that he would experience an increase in the pain during the course of the day and would wake up with very painful and stiff wrists and knees the next morning. By following this program with the Voltaren cream, the patient found that the pain that he would otherwise have experienced was reduced considerably, but there was still an ache.

Since having first tried the cream according to the present invention, the patient now follows the same program but using the cream rather than Voltaren cream. The patient has found that he experiences no pain or ache at all after playing bowls by following this program with the cream containing the active composition A prepared according to Example 1 of the present invention.

The patient also now applies the cream when his fingers, wrist or knees swell up. The cream works more quickly than the Voltaren cream. Moreover, the relief is greater and longer lasting. He has reduced the Voltaren tablets that he takes from two to one per day, and no longer uses the Voltaren cream.

Comments and Observations

The patient was very skeptical as to the benefits of using the cream containing active composition A prepared according to Example 1 of the present invention.

He tried the cream after his wife suggested he do so. The patient is now a firm believer that the cream prepared according to the process of the present invention is far superior to the Voltaren cream that he had previously been using.

In the patient's words, the cream relieves the symptoms of the rheumatoid arthritis, more quickly than the medication that he had been using, and the effect lasts longer. He says also that the cream is easier to apply.

The patient has further reduced his intake of Voltaren tablets from two to one per day and has reduced his intake of Methotrexate tablets by 50%.

Example 19A

Skin Complaint

The patient is a retired 68 year old Australian female. The patient's skin was wrinkly and her eyelids had drooped to the extent that she could not see properly. The patient is a smoker and she has spent a great deal of her life in the sun.

Previous Medication and Results

The patient never used any skincare products when she was a young woman. When she was young the patient's skin was oily, but as she became older she found that her skin tended to become dry. As a result she began to use a moisturiser, purchasing whatever brand she found in her local supermarket.

Products Supplied

The patient has been treated by applying the composition prepared according to Example 1. The composition of Example 1 has been applied to the patient's face, in one or more coats, retained for 30 to 60 minutes and then removed by washing. This has been applied approximately once every two days. She has also applied Compositions E and M (prepared according to Examples 8 and 3 respectively) in accordance with the above steps for applying A. She has also applied layers of each different composition A, E and M (waiting for drying of each layer before applying the next) and then removing after about 30 minutes.

Results

The patient has found that the products prepared according to the present invention have reduced the dryness of her skin and returned her skin to what she considers a "normal" condition.

Her wrinkles have smoothed out considerably, especially around her eyes, and she no longer has any problems with her sight as her eyelids no longer droop. The skin around her neck, face and chest has tightened with the result that she looks and feels much younger.

Comments and Observations

The patient used to call herself the "frilled neck lizard". However, since using the products prepared in accordance with the process of the present invention, her husband and friends have noticed that she is looking much younger. As a result of her improved appearance her confidence has soared.

Example 19B

The Disease

The 68 year old retired Australian female who is the subject of the previous Example 19A, has also suffered from PMR or poly-myalga-rheumatica for approximately 14 years. It affects her whole body, causing her body to be generally aching but in particular she experiences pain in her neck, shoulders, hands, knees and ankles The pain became so severe that she had to give up playing golf six years ago.

Shortly before the patient was diagnosed with PMR she had contracted Ross River fever.

Previous Medication and Results

For the first six months after she was diagnosed as suffering from PMR the patient was on prescribed anti-inflammatory drugs. However, these caused stomach pains and she was rushed to hospital one night suffering from severe stomach pains. As a result she was taken off anti-inflammatory drugs.

The patient was subsequently prescribed Panamax, a stronger form of Panadol, but this was not effective to relieve her pain.

None of the doctors who have examined the patient have ever suggested that she use a cream. However, about five years ago, the patient started using Voltaren cream, which her husband was using for relief of pain caused by his rheumatoid arthritis. The first occasion that she used Voltaren cream was while she was on a trip and was in quite severe pain. She went into a chemist's and purchased the Voltaren cream.

Since then the patient regularly used Voltaren cream to relieve the pain in her neck, shoulders, hands, knees and ankles She would apply the Voltaren cream in the morning after waking up if the pain was unbearable. The Voltaren cream gave her relief after about 20 minutes and would generally last all day.

Towards the end of 2001, the patient was prescribed a drug called CELEBREX as a painkiller. This drug proved to be effective and did not cause the same side-effects as the anti-inflammatory drugs she had used when she was first diagnosed with PMR. Since taking CELEBREX the patient is now able to play nine rounds of golf, although she experiences quite severe pain the next day.

At the beginning of 2003, the patient was taken off CELEBREX because of the adverse effect on the medication she was taking following a heart attack. She had been prescribed a different heart tablet, but that seemed to cause even more problems. At the beginning of February, the patient was put back on CELEBREX. Her doctor is currently evaluating the results of the various changes in the medication prescribed since she commenced using CELEBREX.

The CELEBREX was effective as a painkiller, such that the patient did not need to use the Voltaren cream as frequently as she had before, but only when the pain became unbearable which was not often.

Products Supplied

The patient started using the cream containing composition A prepared according to Example 1 above, in the second half of January of 2003 when the pain was becoming severe.

Results

The patient used the cream containing composition A prepared according to the process of Example 1 once per day when she got up in the morning and has found it effective in controlling the pain in her neck, shoulders, hands, knees and ankles Example 20

Skin Complaints

The patient is a 65 year old retired Australian male who has suffered from psoriasis for approximately 18 years. For the first 3 years only his scalp was affected, but from 1988 the patient began to suffer psoriasis mainly on his hands and arms but at times on his face as well, and occasionally on his legs. Generally, when it flares, the psoriasis starts between the fingers and spread up his hands and arms. A large red "birthmark" appeared on the right-hand side of his face, becoming a permanent feature although it varied in colour depending on whether he was suffering from the manifestation of psoriasis on his hands and arms or not. The psoriasis flares when he is exposed to heat, dirt and dust and especially when he is doing manual work outdoors. The patient has also observed that his condition is exacerbated when he is stressed. In addition, it tends to get worse when he goes from a cool to a warmer climate. The skin on his arms is particularly affected and has the appearance of having been scalded when the psoriasis flares.

The only began to suffer from psoriasis when he was a prison officer. He found this job particularly stressful; he did not regard the various hazardous incidents in which he was involved during his previous navy career, including a number of incidents in which his life was at risk both during active service and whilst performing other duties as a diver, as being stressful. The psoriasis would invariably break out during the summer or when he was on leave. The patient believes that he was more stressed when he was on leave from his job as a prison officer than when he was on duty.

The patient's greatest problem is the itchiness when the psoriasis flares, causing him to want to scratch and rub. When the itchy area is rubbed or scratched, the area becomes more itchy and little pustules appear on the skin in the form of individual circles, collectively forming larger circles. The surface of the pustular area become raised. If the pustules are broken by scratching a clear white fluid is exuded, which the patient has been told by various doctors is lymph. The pustular areas spread rapidly and erratically.

Before he was first treated by products prepared according to the process of the present invention, the itchiness used to drive the patient crazy. At night, the patient would put socks over both hands to stop himself from scratching. The patient believes that it is the itchiness and the resultant scratching and rubbing that causes the psoriasis to spread.

On one occasion about 8 years ago, an outbreak on his right hand put the patient out of action for 3 months due to the dressing that had been put on by a doctor rubbing the skin while he worked. He had been told not to use his hand until it had healed, but he had not waited for this to happen. As a result his hand became septic.

Before he was first treated by products prepared according to the process of the present invention towards the end of 2001, the patient had a pronounced red "birthmark" on the right-hand side of his face. This blemish had appeared approximately 10 years previously, and it became progressively larger over the years. By the time he was first treated it covered almost 80% of the upper right-hand side of his face.

Previous Medication and Results

The patient's daughter has suffered from psoriasis since the age of 7, some 10 years before the patient himself was first afflicted or displayed any of the symptoms associated with the disease. The patient's daughter suffered seriously as a young girl, as a result of which the patient became very familiar with the disease, the various treatments and the fact that there was little that conventional medicine or treatments could do to effectively control or alleviate the skin condition resulting from psoriasis. Indeed, in the patient's words, conventional treatment and products "did nothing" for the patient's daughter at all.

During the period when he only suffered from psoriasis of the scalp, the patient would wash his hair with a number of different bitumen based shampoos recommended by the various doctors whom he saw. During the first few years when he began to suffer from psoriasis of the hands and arms, the patient visited many doctors who recognised his condition as being psoriasis. However, none of them could be more specific as to the type of psoriasis and were unable to provide or recommend an effective treatment. During the period that he has suffered from psoriasis, the patient has used various products, none of which provided effective relief or any degree of control, and he had simply learnt to live with his condition by the time that he was first treated with products prepared according to the process of the present invention.

Generally, the patient would use several OTC or prescription products at the same time. However, when the psoriasis was really firing neither, or both if used together, had any noticeable effect. The only effective relief when the psoriasis was really firing was obtained by immersing his hands and forearms in a bucket of iced water.

Previous Medication Results

The lotions and creams containing products prepared according to the process of the present invention are the only products that have given effective relief from the itchiness and spreading of the pustules when there has been a psoriatic flare up.

Products Supplied

The patient was initially provided with lotions containing products prepared according to Examples 1 and 2 respectively then from February 2002 with various creams, which the patient generally applies whenever the psoriasis flares. The standard psoriasis cream supplied to the patient contains 60% H and 40% B with sweet almond oil and beeswax.

During the course of 2002, the patient was treated by applying different products prepared according to the process of the present invention, the strengths of those products being varied.

Results

The patient's psoriasis generally flares up very quickly without warning, generally between the fingers. The itchiness builds up very quickly, and the skin becomes red and angry, and pustules form and spread. When an outbreak occurs, the patient applies the lotion to the affected area.

The effects of the application lotion are noticeable almost immediately. The itchiness immediately vanishes and the redness and inflammation is significantly reduced (at least by half) within 10 minutes. If the patient is working when the psoriasis first flares, after the itchiness has subsided, that is within a couple of minutes of applying the lotion, the patient will apply the cream. This appears to the patient to act as an "adhesive carrier" retaining the active ingredients in the cream within and on the surface of the skin.

When no lotion is available, the patient will use the cream, which he keeps refrigerated. The current creams provided don't go off, due to the addition of a preservative. Even so, the patient keeps the cream in the fridge as the application of cream, when no lotion is available, gives relief more quickly if cold. When cream is used in place of lotion the itchiness does not disappear immediately but only after 1 or 2 minutes.

If the patient is not working he now does not apply any cream immediately until the area dries. If he does not apply the cream at all, the skin eventually becomes itchy again, although it is not nearly as powerful as the initial itch when the psoriasis first fires.

The patient has also found that outbreaks tend to be less often and less severe. This is because he often applies the cream when he is working to inhibit a flare up. When psoriasis does flare up this is only because he has not been using the cream. The reason the patient doesn't use the cream continuously is due solely to him running out of it from time to time.

Before starting to use lotions and creams containing products prepared according to Examples 2 and 3 of the present invention, the patient's skin was initially red and rough on those parts of his arms where he had frequent outbreaks of psoriasis and resembled a healed burn. Since using the products of the present invention the skin has become much softer, both in the areas that were rough and red and those that were "normal".

The patient also applies the lotion to minor cuts and abrasions and has found that it has an antiseptic effect.

Comments and Observations

The patient was originally very skeptical. However, when it was suggested to him that he could treat and remove the ugly red lump on the right side of his face that had only appeared when he first suffered from psoriasis, he had totally rejected the possibility that lotions containing products prepared according to the present invention would have any effect.

During the first treatment, the "birthmark" broke up into five distinctive areas. Eventually after weekly treatment over 5 months, during which different strengths and combinations of the products prepared according to the process of the present invention were applied, the "birthmark" almost completely disappeared. Since then, when the psoriasis does fire the "birthmark" again becomes noticeable, but one application of the cream results in it disappearing within a few hours.

The patient had the first treatment for psoriasis on his hands and arms, which had just flared up that day, within a couple of weeks of the first treatment on his face. There was noticeable relief after the first treatment.

Example 21

Skin Complaints

The patient's skin was showing the normal signs of old age. Before the commencement of treatment, her face was very wrinkly and her cheeks had drooped to quite a large extent.

The patient also suffered from the long term effects of a previous car accident which had resulted in a lack of blood circulation in her legs and feet which had made walking difficult and painful and had also caused splitting and bleeding of her heels.

Previous Medication and Results

The patient has not worn makeup for many years.
The only cream the patient applied was Vitamin E.

Products Supplied

Since September 2002 the patient applied a lotion containing active Composition A (prepared according to Example 1) every second night before going to bed.

The patient has also been using a cream containing active composition "A" on her feet, applying it every second night.

Results

The skin on the patient's face has tightened and the wrinkles have noticeably reduced.

The patient's heels have recovered significantly and no longer split and bleed.

The soap has also helped her skin leaving it feeling fresh and clean and reducing the lines on her face.

Example 22

Skin Complaints

The patient is a 71 year old female whose skin was showing signs of ageing and blackheads and pimples were a problem. Throughout her life she had spent a lot of time in the sun and she had not cared or paid much attention to her skin.

Previous Medication and Results

The patient had not used anything specific in the past. She had used Pond's cream quite often. None of these products had any effect in reducing or preventing the aging of her skin.

Products Supplied

The patient has received a facial on a weekly basis involving the application of one coat of composition A (undiluted), allowing coat A to dry and applying another coat of A, allowing that second coat to dry and applying two coats of composition C (undiluted) and two coats of composition E (undiluted) allowing each coat to dry before application of the next coat. Then after about 3060 minutes, washing all coats off with warm water. Alternatively, the patient received a facial comprising one coat of each of A, C and E (directly applied as undiluted).

Results

The first results that the patient noticed were the deep ruts near her eyes began to flatten out. The general condition of her skin improved and blackheads and pimples were less of a problem.

The deep "bag on a bag" under her right eye also disappeared.

The firmness and texture of her skin has improved and the wrinkles in her cheeks have flattened out significantly and left her skin glowing and feeling fresh.

Example 23

Skin Complaints

The patient is a 39 year old female who had thought that she had any skin problems and thought that her skin, though sensitive, was in good condition.

The patient had however suffered discomfort from her feet that regularly swell up and cause her pain.

She also has varicose veins on her legs and has had sores on her back.

Products Supplied

The patient started having a weekly facial in October of 2002. The facial involved the application of layers of compositions A, C and E as set out in Example 22, or alternatively one layer of A, then after drying one layer of undiluted composition M or C.

The patient was also provided with a cream containing active composition M 60% w/w (produced according to Example 3).

Results

The facials have resulted in cleaner skin and has reduced the lines in her face. The fine lines have disappeared and the heavier ones have become less obvious.

The cream has had a similar beneficial effect to other lotions containing compositions of the present invention. The patient now applies M before applying weak solutions of the other lotions containing compositions of the present invention, and experiences no discomfort in treating her face.

The facials have given the patient's face a lift and eradicated the bags under her eyes. These effects could be seen from the first application.

A scar near her left eye that was very deep has almost disappeared.

The patient has further applied the facial lotions to the varicose veins on her legs and they have become less obvious after only 3 weeks.

Comments and Observations

The patient finds that the treatments tend to last for at least three days before she wants another facial.

Another change that the patient has noticed since using soap containing an active composition of the present invention with her family is that they have been less susceptible to sunburn.

Example 24

Skin Complaints

The patient is a 45 year old female who suffered severe scarring on her face as a result of a car accident around 10 to 12 years ago.

The skin on both sides of her neck was discoloured (purple and white in patches) and rough with the texture of sandpaper.

The patient's left cheek drooped so badly that it looked as though she had suffered from a stroke and she was unable to smile.

The patient was developing wrinkles and a double chin.

The patient also suffers from pain in the top of her right leg as a result of the accident.

Previous Medication and Results

Since recovering from the accident, the patient had not used any particular cosmetics recently except for sorbolene for her face.

The patient had used codeine to provide relief from her back pain

Products Supplied

The patient has been having weekly facials using a composition of the present invention since 3 Sep. 2001. These comprised the application of at least one coat of undiluted composition C to her face, leaving 3090 minutes and then removing by washing in warm water.

The patient has also been using a cream containing compositions A and C (in a ratio of 9:1) prepared according to Examples 1 and 6, with beeswax and sweet almond oil, which she applies to the top of her leg when pain occurs.

Since September 2002, apart from sorbolene, the patient has only been using lotions, creams and soaps containing compositions of the present invention.

Results

The scars on the patient's face, neck and throat have reduced significantly. The scars on her face and neck have become so subtle that you need to look to see them, and even the scars on her throat that had been very obvious previously are now barely visible.

Her left cheek and the side of her mouth that were drooping have tightened and are now "back where they should be". Her face no longer looks as though she has had a stroke and her skin has become firm and her wrinkles are significantly reduced. These changes became noticeable after only 2 facials. Her skin has gone from having a sandpaper texture to feeling smooth, and her colouring has returned to normal.

The condition of her skin since she has been having the facials and using soap has improved. It has become softer and pimples and blackheads have become very rare.

The patient applies the cream to her upper leg and lower back when the pain arises. It has an immediate effect at lessening the pain, and by the following day the pain will have gone. She only needs to use the cream once for the pain to be relieved in her back and leg.

Comments and Observations

In the past the patient tended to hide away from the world and basically she led a reclusive existence. Now, she no longer feels as though the scarring and the condition of her skin and face defines her as a person and she has started to live a more "social" life again. She is now feeling much more confident and able to face the world.

Example 25

All of the fingertips on the patient's right hand were accidentally burnt by caustic solution whilst the patient was cleaning the walls in the kitchen of his cafe.

The patient took no immediate treatment other than to run cold water from the tap over his fingers. He continued working for approximately an hour before going home. When he arrived home, the patient ran water from a tap over his fingers and then dipped his fingers in a lotion which comprised a mixture of active compositions A and M (prepared according to Examples 1 and 3 respectively the active filtrates of each being mixed together in a 9:1 ratio).

The middle finger was the most severely burnt—there were two reddish "blood" blisters and a "split", where the skin had broken like a cut for 3 to 4 mm. The other fingers did not blister but were very red and painful, and tender.

On immersing his fingertips in the lotion the patient experienced immediate relief, with the burning sensation virtually disappearing altogether.

After a few hours the fingers started stinging again, and the patient applied a cream containing A and M which relieved the burning sensation within a couple of minutes. Over the course of the next couple of days, the patient applied the cream a number of times to relieve the sting as it gradually came back.

By Wednesday 8 January all of fingertips were completely healed. The split on the middle finger had left a visible scar which disappeared after about 2 weeks, even though the finger was burnt again during that period.

Saturday 11 Jan. 2003

The patient burnt his right index finger in boiling oil (at approx 180° C.) in his cafe at about 7 o'clock in the evening. The pain was a lot more severe than that caused by the caustic burn a few days earlier.

The patient applied the cream containing a mixture of A and M immediately after he burnt his finger. The cream did not relieve the pain. The patient then applied the lotion comprising a mixture of undiluted A and M in a ratio of 9:1. When the patient got home at about 9 o'clock, the finger was irritating but not painful. The patient had a big raised white blister, with a build-up of fluid underneath. He applied some of the cream.

On the morning of the next day, the blister was very flat and soft, with no build-up of fluid under the blister. There was no pain or irritation. The patient applied some of the cream and then went to work. He did not apply any lotion or cream during the rest of the day.

By the next morning (i.e. after 36 hours) the blister had gone and the skin colour had returned to normal. There was no sign of the burn at all.

Tuesday 14 Jan. 2003

In the afternoon, the patient deliberately burnt the index and middle fingers of his right hand, by dipping them into a vat of boiling oil at a measured temperature of 162° C., filming the event and the subsequent treatment on video.

The result was two painful fingers. After about 10 mins, the patient dipped his fingers in the lotion containing active compositions A and M in a ratio of 9:1, which was at room temperature (measured at 30° C.) for 60 seconds. The patient experienced immediate relief. However, on removing the fingers from the container holding the lotion the pain came back, so the patient put his fingers back into the same lotion. When he took the fingers out again the pain had diminished considerably.

During the evening the patient dipped his fingers in the lotion once and applied a cream also containing active compositions A and M in a ratio of 9:1 several times. His fingers were still painful two hours later and there was some blistering of the skin. Both fingers were slightly swollen with a build-up of fluid under the skin. By night time, the pain had gone altogether, and the blistering had not increased.

By about 5 o'clock the next morning, the patient's fingers weren't painful or even tender, and the degree of blistering had not changed.

The patient applied the cream several times during the day. At no time did he experience any pain or irritation.

By the afternoon the skin on the burnt areas of the finger had become hard. In the evening the white colouration began to recede.

When he awoke the next morning the white skin had almost disappeared.

By midday the blister on the patient's index finger had disappeared and the finger was almost back to normal. The white colouration of the middle finger was split into two areas.

By 3 o'clock, 48 hours after he had burnt his fingers, the patient's index finger was back to normal, and there was sign that it had been burnt. The white colouration of the middle finger was almost completely gone.

Example 26

Skin Complaints

The patient, a 35 year old female, has suffered from psoriasis since the age of 7. The most recent severe psoriasis outbreak has been on her scalp.

Previous Medication and Results

After the patient was first afflicted with psoriasis, she devoted an enormous amount of time and energy to finding a cure, without success.

The products that the patient has used include cortisone creams, tar based creams and shampoos and other steroid creams. These products have not inhibited or prevented renewed outbreak of psoriasis although they have enabled the patient to control it.

Products Supplied and Results

The patient has used a lotion which is pure composition H with grapefruit seed extract preservative and also psoriasis soap containing composition H prepared according to Example 2 present in 10% w/w. Since she has most recently had problems with her scalp, she has been using the soap, as it is easier to use than the oil. She has been using the soap once a week and when she has an outbreak to control the psoriasis. The itch and scale disappears in a more efficient manner than has been the case previously with other products.

Comments and Observations

The patient is both impressed and happy with the products of the invention since they have been better at controlling her psoriasis than other products.

She is particularly pleased that the products are completely natural as this gives her greater peace of mind.

Example 27

Skin Complaints

The patient, a 60 year old male has suffered from mild psoriasis, which he believes is stress related, for over 30 years. He experiences the symptoms three or four time a year, on his scalp and the back of his neck, and occasionally minor symptoms on his legs.

Previous Medication and Results

The patient has used prescribed ointments and creams and lotions which have been recommended by his doctor as giving relief.

The patient found that these products gave him little relief

Products Supplied

The patient was provided with psoriasis soap containing composition H prepared according to Example 2 present in 10% w/w, and with psoriasis lotion which is pure composition H with grapefruit seed extract preservative.

Results

The patient has found that the soap itself controls the symptoms, and does not need to use the lotion. He has found that the frequency and intensity of the symptoms has diminished.

Example 28

The patient presented with his left foot having the fourth toe as gangrenous, the doctor having determined that amputation would be required. The patient was treated by topical application of a lotion prepared containing 50% each of undiluted active filtrate composition A and active filtrate composition M of the present invention every morning. The lotion was applied to the affected area, allowed to dry and washed off after about 60 minutes. This topical application continued for two weeks. The patient then applied a cream containing A and M in a ratio of 1:1 once a day, which remained on the skin generally overnight.

Within 2 weeks the gangrenous flesh had disappeared and healthy flesh was appearing. Good blood flow was restored to the toe. The patient has retained his toe and it appears and functions as fully normal.

Example 29

The female patient presented with very poor and lifeless skin, bloodshot eyes and was treated with a composition derived from a mixture of peach flesh, grapefruit flesh and apricot flesh pulp to which 10% w/w sodium bicarbonate had been added. The mixture had then been frozen, thawed and filtered and the resulting active filtrate composition was applied to the patient's skin. The composition was applied directly to the skin of the face and neck for 60 minutes and then removed by washing with warm water. This was repeated once every two days and within one the patient's skin was of excellent clarity, had exfoliated and blood circulation was excellent.

Example 30

1. Take normal fresh pawpaw, not unripened or overripe.
(a) Remove skin and outer layer of hard flesh.
(b) Remove seeds.
2. Take 300 g of pawpaw flesh and place in Pyrex bowl.
3. Pulp pawpaw flesh with a hand-mixer.
4. Place pulped pawpaw flesh into the top pan of a stainless steel double-boiler.
5. Fill the bottom pan of the double-boiler with water to about two-thirds full.
6. Place bottom pan of the double-boiler on stove or hot plate and bring to the boil.
7. Place the top pan containing the pulped pawpaw flesh on top of the bottom pan.
8. Continue heating the bottom pan whilst manually stirring the pulped pawpaw flesh in the top pan using a wooden spoon until the temperature of the pulped pawpaw flesh reaches about 55° Celsius.
9. Preheat 1 liter Pyrex bowl to about 55° Celsius.
10. Transfer heated pulped pawpaw flesh to heated Pyrex bowl.
11. Add 30 gm of sodium carbonate to heated pulped pawpaw flesh.
12. Stir heated pulped pawpaw flesh vigorously with a wooden spoon until effervescence ceases.
13. Beat heated pulped pawpaw flesh vigorously using an electric mixer until texture is that of a smooth cream. This takes 20 to 40 seconds.
14. Pour the heated pulped pawpaw flesh into a container.
15. Put lid on container.
16. Place container in deepfreeze.
17. After the contents of the container have frozen remove container from deep freeze.
18. Allow liquor to filter through calico for 12 to 24 hours and collect in Pyrex bowl.
19. The collected liquor (filtrate) is the active raw composition demonstrating efficacy and producing the beneficial effects.

The resulting active composition can be formulated as set out in respect of Example 1 and has the same beneficial effects as set out in items 1 to 7 of Example 1.

Notes

1. The heating step can be effected in a microwave rather than a double-boiler.
2. The optimum temperature is 55° C. and the preferred temperature range is 50° C. to 60° C. Product with beneficial properties can be created if the temperature is between 40° C. and 100° C.
3. The proportion of sodium carbonate can be varied from 1% to 40% of the pulped flesh by weight. The lower proportion of sodium carbonate is more suitable for persons with extremely sensitive skin. As the proportion of sodium carbonate increases the raw product becomes progressively more likely to burn the skin.
4. The pH of the final product when the weight of sodium carbonate is 10% of the weight of the pulped pawpaw flesh is approximately 8.
5. The freezing step may be omitted, but in some cases, the product formed from adding sodium carbonate to the heated pulped flesh becomes gellike and the filtration of the liquor is more difficult.

Example 31

1. Take potatoes and peel them to remove skin.
2. Take 300 gm of potato and place in Pyrex bowl.
3. Pulp potato with a hand-mixer.
4. Place pulped potato into the top pan of a stainless steel double-boiler.
5. Fill the bottom pan of the double-boiler with water to about two-thirds full.
6. Place bottom pan of the double-boiler on stove or hot plate and bring to the boil.
7. Place the top pan containing the pulped potato flesh on top of the bottom pan.
8. Continue heating the bottom pan whilst manually stirring the pulped potato in the top pan using a wooden spoon until the temperature of the pulped potato reaches about 55° Celsius.
9. Preheat 1 liter Pyrex bowl to about 55° Celsius.
10. Transfer heated pulped potato to heated Pyrex bowl.
11. Add 30 gm of sodium bicarbonate (as purchased in a supermarket) to heated pulped potato flesh.
12. Stir heated pulped potato vigorously with a wooden spoon until effervescence ceases.
13. Beat heated pulped potato vigorously using an electric mixer until texture is that of a smooth cream. This takes 20 to 40 seconds.

14. Pour the heated pulped potato into a container.
15. Put lid on container.
16. Place container in deepfreeze.
17. After the contents of the container have frozen remove container from deepfreeze.
18. Allow liquor to filter through calico for 12 to 24 hours and collect in Pyrex bowl.
19. The collected liquor (filtrate) is the active raw composition demonstrating efficacy and producing the beneficial effects.

The resulting active composition from the pulped potato can be formulated according to suggestions 1 to 4 in respect of Example 1 above. Further the beneficial effects of the composition resulting from the pulped potato are the same as set out in items 1 to 7 for Example 1. Further, the beneficial effect of skin whitening has been observed in respect of composition resulting from processing potato according to this example.

Notes

1. The heating step can be effected in a microwave rather than a double-boiler.
2. The optimum temperature is 55° C. and the preferred temperature range is 50° C. to 60° C. Product with beneficial properties can be created if the temperature is between 40° C. and 100° C.
3. The proportion of sodium bicarbonate can be varied from 1% to 40% of the pulped flesh by weight. The lower proportion of sodium bicarbonate is more suitable for persons with extremely sensitive skin. As the proportion of sodium bicarbonate increases the raw product becomes progressively more likely to burn the skin.
4. The pH of the final product when the weight of sodium bicarbonate is 10% of the weight of the pulped potato flesh is approximately 8.
5. The freezing step may be omitted, but in some cases, the product formed from adding sodium bicarbonate to the heated pulped flesh becomes gellike and the filtration of the liquor is more difficult.

Example 32

Formulation

1. Take 100 g of macadamia oil or emu oil or any other nut or seed or animal oil.
2. Add 18% w/w (18 g) natural beeswax.
3. Add 5% w/w (5 g) glycerin.
4. Add 10% w/w (10 g) cocoa butter.
5. Add the solid cocoa butter and beeswax and glycerin to the oil, heat slowly and gently with mixing until all solids have melted. Cool the heated liquid to about 45.degree. C. and add 60% w/w (60 g) of active composition prepared according to any one of Examples 1 to 5 above.
6. Mix continuously to a smooth creamlike consistency.

Note

The amount of active added will depend upon which disorder or indication the cream is intended to be used. For example, if it is intended to create an eczema cream, then about 10% to 20% w/w of the active is added.

Example 33

1. Take a moisturising cream such as sorbolene in an amount of about 250 g.

2. Add in active prepared according to the present invention in an amount of between about 5% to 60% w/w.

Note

The active can be added in the final filtrate, or in the form of the fruit whip-like mixture resulting after addition of the mild base and ceasing of effervescence.

Example 34

1. Standard saponification process is carried out, heating a mixture of oil and lye (NaOH).
2. As the temperature decreases, an active composition of the present invention is added in an amount of 10% w/w of the saponification mixture. This addition occurs at about 35-36° C., prior to the actual tracing which starts at about 32° C.

The invention claimed is:

1. A composition obtainable by a process comprising the steps of:
   a) pulping paw paw fruit to form a viscous liquid pulp;
   b) heating said pulp up to a temperature in the range of 50° C. to 60° C.; and
   c) mixing between 5% and 15% w/w of a mild base with the heated pulp of step (b) while said pulp has a temperature in the range of 50° C. to 60° C.

2. The composition of claim 1, wherein about 10% w/w of mild base is mixed with the heated pulp of step (b).

3. The composition of claim 2, wherein said pulp of step (b) is heated to 55° C. and said pulp of step (c) has a temperature of 55° C.

4. The composition of claim 3, wherein the pH of the composition is from 7.5 to 9.5.

5. The composition of claim 1, wherein the process further comprise filtering the mixture of step c) to remove solids and retaining the liquid filtrate.

6. The composition of claim 1, wherein the base comprises a bicarbonate and/or a carbonate.

7. The composition of claim 6, wherein the base comprises a water-soluble alkali metal bicarbonate salt and/or a water-soluble alkali metal carbonate salt.

8. The composition of claim 7, wherein the base comprises $CO_3^{2-}$, $CN^-$, $NH_3$, $HS^-$, $HCO_3^-$, $CH_3CO_2^-$, $NO_2^-$, $F^-$, $H_2PO_4^-$, $SO_4^{2-}$, $NO_3^-$, $Cl^-$, $Br^-$, $I^-$, $HSO_4^-$ and/or $ClO_4^-$.

9. The composition of claim 1, further comprising a formulation ingredient selected from the group consisting of emulsifiers, stabilizers, anti-oxidants, coloring agents, moisturizers, surfactants, emollients, conditioning agents, essential oils, fragrance, and combinations thereof.

10. A method of treating a dermatological disorder in a subject in need thereof comprising topically applying an effective amount of the composition of claim 1 to the skin of said subject.

11. A process for preparing the composition of claim 1 comprising the steps of:
    a) pulping paw paw fruit to form a viscous liquid pulp;
    b) heating said pulp up to a temperature in the range of 50° C. to 60° C.; and
    c) mixing between 5% and 15% w/w of a mild base with the heated pulp of step (b) while said pulp has a temperature in the range of 50° C. to 60° C.

12. The process of claim 11, wherein the base comprises a bicarbonate and/or a carbonate.

13. The process of claim 11, wherein the base comprises a water-soluble alkali metal bicarbonate salt and/or a water-soluble alkali metal carbonate salt.

14. The process of claim 12, wherein the base comprises $CO_3^{2-}$, $CN^-$, $NH_3$, $HS^-$, $HCO_3^-$, $CH_3CO_2^-$, $NO_2^-$, $F^-$, $H_2PO_4^-$, $SO_4^{2-}$, $NO_3^-$, $Cl^-$, $Br^-$, $I^-$, $HSO_4^-$ and/or $ClO_4^-$.

\* \* \* \* \*

UNITED STATES PATENT AND TRADEMARK OFFICE
CERTIFICATE OF CORRECTION

PATENT NO. : 10,143,716 B2
APPLICATION NO. : 14/178420
DATED : December 4, 2018
INVENTOR(S) : Thomas James McArthur Page 1 of 1

It is certified that error appears in the above-identified patent and that said Letters Patent is hereby corrected as shown below:

In the Claims

In Claim 3, Column 30, Line 32, delete "claim 2," and replace with --claim 1,-- therefor.

Signed and Sealed this
Twenty-sixth Day of February, 2019

Andrei Iancu
*Director of the United States Patent and Trademark Office*